United States Patent [19]

Clitherow et al.

[11] 4,323,566
[45] Apr. 6, 1982

[54] TRIAZOLE ACYLAMINES, PHARMACEUTICAL COMPOSITIONS THEREOF AND METHOD OF USE THEREOF

[75] Inventors: John W. Clitherow, Sawbridgeworth; Barry J. Price, Hertford; John Bradshaw; Michael Martin-Smith, both of Ware; John W. M. MacKinnon, Royston; Duncan B. Judd, Ware; Linda Carey, Royston, all of England

[73] Assignee: Glaxo Group Limited, London, England

[21] Appl. No.: 125,847

[22] Filed: Feb. 29, 1980

[30] Foreign Application Priority Data

Mar. 2, 1979 [GB] United Kingdom ............... 07421/79

[51] Int. Cl.³ .................. C07D 403/12; A61K 31/41; C07D 403/14
[52] U.S. Cl. .......................... 424/248.51; 424/248.56; 424/258; 424/263; 424/267; 424/269; 424/270; 544/124; 544/127; 544/128; 544/132; 544/133; 546/169; 546/201; 546/193; 546/194; 546/267; 546/276; 548/200; 548/214; 548/267
[58] Field of Search .................. 548/267, 200, 214; 546/276, 210, 169, 201, 193, 194; 424/248.56, 263, 269, 267; 544/132, 124, 127, 128, 133

[56] References Cited

U.S. PATENT DOCUMENTS

| | | | |
|---|---|---|---|
| 3,233,302 | 11/1980 | Martin-Smith et al. | 546/210 |
| 4,128,658 | 12/1978 | Price et al. | 424/285 |
| 4,145,546 | 3/1979 | Brown et al. | 544/310 |
| 4,154,834 | 5/1979 | Brown et al. | 544/320 |

FOREIGN PATENT DOCUMENTS

| | | | |
|---|---|---|---|
| 867105 | 11/1978 | Belgium | 549/59 |
| 867106 | 11/1978 | Belgium | 280/326.1 |
| 875846 | 4/1979 | Belgium | 548/267 |
| 1419994 | 1/1976 | United Kingdom | 544/324 |
| 2003471 | 3/1979 | United Kingdom | 546/276 |

*Primary Examiner*—Robert T. Bond
*Attorney, Agent, or Firm*—Bacon & Thomas

[57] ABSTRACT

The invention relates to compounds of the general formula (I)

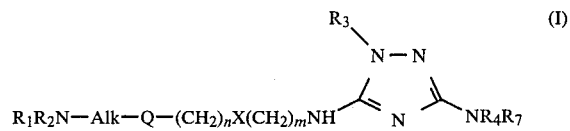

and physiologically acceptable salts, hydrates and bioprecursors thereof, in which $R_1$ and $R_2$, which may be the same of different, each represent hydrogen, $C_1$ alkyl, cycloalkyl, alkenyl, alkynyl, aralkyl, trifluoroalkyl, or alkyl substituted by hydroxy, alkoxy, amino alkylamino dialkylamino or cycloalkyl or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl groups or a hydroxy group and/or may contain another heteroatom which is oxygen or sulphur;

Alk represents a straight or branched alkylene chain of 1 to 6 carbon atoms,

Q represents a furan or thiophene ring in which incorporation into the rest of the molecule is through bonds at the 2- and 5- positions, the furan ring optionally bearing a further substituent $R_6$ adjacent to the group $R_1R_2N$-Alk, or Q represents a benzene ring in which incorporation into the rest of the molecule is through bonds at the 1- and 3- or 1- and 4- positions;

$R_6$ represents halogen or $C_{1-4}$ alkyl which may be substituted by hydroxy or $C_{1-4}$ alkoxy;

x represents $-CH_2-$, $-O-$, $-S-$ or

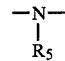

where $R_5$ represents hydrogen or methyl;
n represents zero, 1 or 2;
m represents 2, 3 or 4;
$R_3$ represents hydrogen, alkyl, alkenyl, aralkyl, hydroxyalkyl with at least two carbon atoms, alkoxyalkyl, or aryl, and
$R_4$ represents hydrogen, alkyl, alkenyl or aralkyl and $R_7$ represents the group $COR_8$ where $R_8$ represents hydrogen, alkyl, aryl, aralkyl, alkoxy, heteroaryl or monocyclic heteroarylalkyl or $R_7$ represents the group $SO_2R_9$ where $R_9$ represents alkyl or aryl, or $R_7$ represents the group

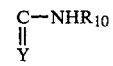

where Y is oxygen or sulphur and $R_{10}$ represents hydrogen, alkyl, cycloalkyl, aryl or aralkyl.

The compounds of formula (I) show pharmacological activity as selective histamine $H_2-$ antagonists.

18 Claims, No Drawings

TRIAZOLE ACYLAMINES, PHARMACEUTICAL COMPOSITIONS THEREOF AND METHOD OF USE THEREOF

This invention relates to novel heterocyclic derivatives having action on histamine receptors, to processes for the preparation thereof, to pharmaceutical compositions containing them and to their use in therapeutics.

Certain novels heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in German Offenlegungsschrift No. 2,734,070, modified by the use of sodium pentobarbitone (50 mg/kg) as anaesthetic instead of urethane, and in conscious dogs equipped with Heidenhain pouches using the method described by Black et al, Nature 1972 236, 385. Furthermore the compounds antagonise the effect of histamine on the contraction frequency of isolated guinea pig right atrium but do not modify histamine induced contractions of isolated gastrointestinal smooth muscle which are mediated via $H_1$-receptors. Certain compounds according to the invention have the advantage of an extended duration of action.

Compounds with histamine $H_2$-blocking activity may be used in the treatment of conditions where there is an advantage in lowering gastric acidity, particularly in gastric and peptic ulceration, as a propylactic measure in surgical procedures, and in the treatment of allergic and inflammatory conditions where histamine is a known mediator. Thus they may be used for example, either alone or in combination with other active ingredients in the treatment of allergic and inflammatory conditions of the skin.

The present invention provides compounds of the general formula (I)

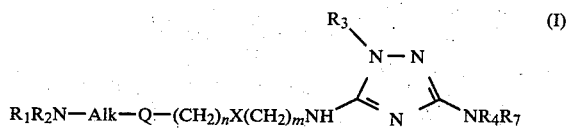

and physiologically acceptable salts, hydrates and bioprecursors thereof, in which $R_1$ and $R_2$ which may the same or different, each represent hydrogen, $C_{1-10}$ alkyl, cycloalkyl, alkenyl, alkynyl, aralkyl, trifluoroalkyl, or alkyl substituted by hydroxy, alkoxy, amino, alkylamino, dialkylamino or cycloalkyl or $R_1$ and $R_2$ may together with the nitrogen atom to which they are attached form a 5 to 10 membered ring which may be saturated or may contain at least one double bond, may be unsubstituted or may be substituted by one or more $C_{1-3}$ alkyl groups, e.g. methyl or a hydroxy group and/or may contain another heteroatom, e.g. oxygen or sulphur;

Alk represents a straight or branched alkylene chain of 1 to 6 carbon atoms, preferably 1 to 4 carbon atoms, Q represents a furan or thiophen ring in which incorporation into the rest of the molecule is through bonds at the 2- and 5-positions, the furan ring optionally bearing a further substituent $R_6$ adjacent to the group $R_1R_2N$—Alk—, or Q represents a benzene ring, in which incorporation into the rest of the molecule is through bonds at the 1- and 3- or 1- and 4-positions;

$R_6$ represents halogen or $C_{1-4}$ alkyl which may be substituted by hydroxy or $C_{1-4}$ alkoxy;

x represents —$CH_2$—, —O—, —S— or

where $R_5$ represents hydrogen or methyl;

n represents zero, 1 or 2;

m represents 2,3 or 4;

$R_3$ represents hydrogen, alkyl, alkenyl, aralkyl, hydroxyalkyl with at least two carbon atoms, alkoxyalkyl or aryl; and $R_4$ represents hydrogen, alkyl, alkenyl or aralkyl, and $R_7$ represents the group $COR_8$ where $R_8$ represents hydrogen, alkyl, aryl, aralkyl, alkoxy, heteroaryl or monocyclic heteroarylalkyl or $R_7$ represents the group $SO_2R_9$ where $R_9$ represents alkyl, or aryl, or $R_7$ represents the group

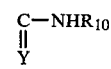

where Y is oxygen or sulphur and $R_{10}$ represents hydrogen, alkyl, cycloalkyl, aryl or aralkyl.

When X represents an oxygen atom or

and n is zero, then Q preferably represents benzene.

The term "alkyl" as a group or part of a group means that the group is straight or branched and, unless otherwise stated, has preferably 1 to 6 carbon atoms, and in particular 1 to 4 carbon atoms, e.g. methyl or ethyl, and the terms "alkenyl" and "alkynyl" mean that the group has preferably 3 to 6 carbon atoms. The term "cycloalkyl" means that the group has 3 to 8 carbon atoms.

The term "aryl" as a group or part of a group preferably means phenyl or substituted phenyl, for example phenyl substituted with one or more $C_{1-3}$ alkyl or alkoxy groups or halogen atoms e.g. fluorine. The acyl portion of an acyloxyalkyl group means an aroyl, aralkanoyl or $C_{1-6}$ alkanoyl group. Examples of acyloxyalkyl groups include acetoxymethyl, formyloxymethyl, benzoyloxymethyl and phenylacetoxymethyl. The term "heteroaryl" generally means a 5 or 6 membered monocyclic ring or 9 or 10 membered bicyclic ring either of which may contain from 1 to 3 heteroatoms selected from oxygen, nitrogen and sulfur, e.g. furyl, pyridyl, thiazolyl, quinolinyl, indolyl or thienyl.

According to one aspect the invention provides compounds according to formula (I) and physiologically acceptable salts, hydrates and bioprecursors thereof, in which $R_1$ and $R_2$ are as defined in formula (I) except alkynyl or alkyl substituted by cycloalkyl;

$R_4$ and $R_7$ are as defined in formula (I) except that $R_8$ is other than heteroaryl and $R_{10}$ is other than cycloalkyl; provided that when X represents an oxygen atom or —$NR_5$— and when n is zero then Q represents benzene.

The invention includes the compounds of formula (I) in the form of physiologically acceptable salts with inorganic and organic acids. Particularly useful salts include hydrochlorides, hydrobromides, sulphates, methanesulphonates acetates, maleates, succinates, citrates, fumarates, tartrates and benzoates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers.

The compounds according to the invention, preferably in the form of a salt, may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients e.g. $H_1$-antagonists.

Thus the compounds according to the invention may be formulated for oral, buccal, topical, parenteral or rectal administration. Oral administration is preferred.

For oral administration, the pharmaceutical composition may take the form of for example, tablets, capsules, powders, solutions, syrups or suspensions prepared by conventional means with acceptable excipients. For buccal adminstration the composition may take the form of tablets or lozenges formulated in conventional manner.

The compounds of the invention may be formulated for parenteral administration by bolus injection or continuous infusion. Formulations for injection may be presented in unit dosage form in ampoules, or in multidose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle e.g. sterile pyrogen-free water before use.

The compounds of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg. to 1 g per day, preferably 5 to 250 mg per day, dependant upon the condition of the patient being treated.

In the compounds according to the invention, preferably the total of m+n is 3 or 4.

Preferably Q is benzene incorporated into the rest of the molecule through bonds at the 1- and 3-positions. In the case where Q is benzene, preferably n is zero, X is oxygen and m is 3 or 4. If Q is furan, substituted furan or thiophen, preferably n is 1, X is sulphur and m is 2.

Preferably $R_1$ represents hydrogen or $C_{1-4}$ alkyl and $R_2$ represents $C_{3-5}$ alkenyl, $C_{5-7}$ cycloalkyl, benzyl, $C_{1-8}$ alkyl or $C_{1-4}$ alkyl substituted by $C_{1-3}$ alkoxy, hydroxy, di-$C_{1-3}$ alkylamino or trifluoromethyl or $R_1$ and $R_2$ together with the nitrogen atom to which they are attached form a ring with 5 to 8 members and optionally containing one double bond and/or substituted by hydroxy or one or two $C_{1-3}$ alkyl group(s). More preferably $R_1$ and $R_2$ are $C_{1-3}$ alkyl, e.g. methyl or $R_1$ and $R_2$ together with the nitrogen atom to which they are attached form a heterocyclic ring which is pyrrolidine, piperidine optionally substituted in the 4-position by $C_{1-3}$ alkyl e.g. methyl or hydroxy, tetrahydropyridine, morpholine, 2,6-dialkylmorpholine, hexamethyleneimine or heptamethylenimine. Most preferably the heterocyclic ring is piperidine.

Preferably $R_3$ represents hydrogen, alkyl or $C_{2-4}$ hydroxyalkyl. More preferably $R_3$ represents methyl.

Preferably the group $NR_4R_7$ represents the group $NHCOR_8$ where $R_8$ represents hydrogen, alkyl, aryl, heteraryl or alkoxy, or the group $NHCONHR_{10}$ where $R_{10}$ represents alkyl, aryl or cycloalkyl. More preferably the group $NR_4R_7$ is the group $NHCOR_8$ where $R_8$ is hydrogen, aryl e.g. phenyl, alkyl e.g. methyl or alkoxy e.g. ethoxy; or the group $NHCONHR_{10}$ where $R_{10}$ is aryl, e.g. phenyl. Most preferably the group $NR_4R_7$ is formylamino or acetylamino.

Preferably Alk is $CH_2$.

A particularly preferred group of compounds of formula (I) are those of formula (II)

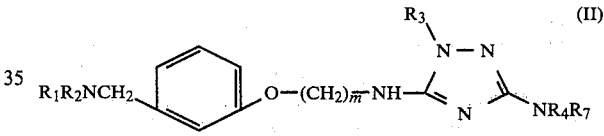

where $R_1$ and $R_2$ are methyl groups or together with the nitrogen atom to which they are attached form a pyrrolidino, piperidino or hexamethyleneimino group; m is 3 or 4, $R_3$ is hydrogen or methyl; and $NR_4R_7$ is a formamide, alkanoylamino, alkoxycarbonylamino, aroylamino or phenylcarbamoylamino group.

(1) N-[1-methyl-5-[[3-[3-(1-piperidinylmethyl)phenoxy]propyl]amino]-1H-1,2,4 triazol-3-yl]formamide (2) N-[5-[[3-[3-(dimethylamino)methyl]-phenoxy]-propyl]amino]-1-methyl-1H,1,2,4-triazol-3-yl]acetamide (3) Ethyl 1-methyl-5-[[3-[3-[(dimethylamino)methyl]-phenoxy]propyl]amino]-1H-1,2,4-triazole-3-carbamate (4) N-[5-[[3-[3-[(dimethylamino)methyl]phenoxy]-propyl]amino]-1-methyl-1H-1,2,4-triazole-3-yl]benzamide (5) N-[5-[[3-[3-(1-piperidinylmethyl)phenoxy]propyl]amino]-1-methyl-1H-1,2,4-triazole-3-yl]-N'-phenylurea and their physiologically acceptable salts.

Of the above mentioned compounds, compounds Nos. (1) and (2) and their salts are particularly preferred.

It will be appreciated that in the methods for the preparation of compounds of formula (I) given below, for certain reation steps it may be necessary to protect various reactive substituents in the starting materials for a particular reaction and subsequently to remove the protecting group. Such protection and subsequent deprotection may be particularly pertinent where $R_1$ and/or $R_2$ in intermediates used to prepare compounds of formula (1) are hydrogen atoms and/or when $R_3$ in intermediates is an alkyl group bearing a hydroxy substituent.

Standard protection and deprotection procedures can be employed, for example formation of phthalimide (in the case of primary amines), benzyl, benzyloxycarbonyl or trichloroethoxycarbonyl derivatives. Subsequent cleavage of the protecting group is achieved by conventional procedures. Thus a phthalimide group may be cleaved by treatment with a hydrazine e.g. hydrazine hydrate or a primary amine, for example methylamine; benzyl or benzyloxycarbonyl derivatives may be cleaved by hydrogenolysis in the presence of a catalyst, e.g. palladium, and trichloroethoxycarbonyl derivatives may be cleaved by treatment with zinc dust.

In describing the processes which may be used for preparing the compounds of formula (1) or intermediates useful in the preparation thereof, any of $R_1$ to $R_{11}$, Alk,Q,X,Y,n and m in the various formulae are as defined in formula (1) unless otherwise stated.

Compounds of formula (I) in which $R_7$ has any of the meanings given for formula I may be prepared by treating an amino triazole

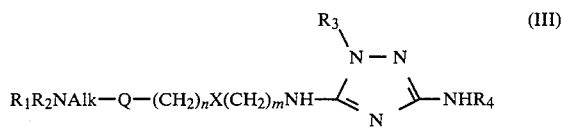

in which $R_1, R_2, R_3$ and $R_4$ are as defined in formula (I) or are groups readily convertible thereto with a reagent capable of replacing the hydrogen atom in the group $NHR_4$ by the group $R_7$.

Thus for example the aminotriazole (III) may be reacted with an activated derivative of either a carboxylic acid $R_8COOH$ or a sulphonic acid $R_9SO_3H$ or with an isocyanate or isothiocyanate $R_{10}'NCY$ in which $R_{10}'$ has any of the meanings defined for $R_{10}$ in formula (I) except hydrogen or represents an alkali metal atom such as potassium or sodium or an alkoxycarbonyl group, e.g. ethoxycarbonyl, to give a compound of formula (I) in which $R_7$ is respectively the group $COR_8$, $SO_2R_9$ or

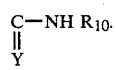

Suitable activated derivatives include acid halides e.g. acid chlorides, alkylchloroformates, acid anhydrides including mixed anhydrides (e.g. acetic formic anhydride), esters such as alkyl esters, ortho esters and (1-alkyl-2-pyridinyl) esters, or derivatives formed from a coupling agent such as carbonyldiimidazole or a carbodiimide such as dicyclohexylcarbodiimide.

The reaction with an acid halide is preferably carried out in the presence of a base e.g. an inorganic base such as sodium hydroxide or an organic base such as triethylamine or pyridine. The reaction with an alkylchloroformate is preferably carried out in the presence of a base, e.g. potassium carbonate or triethylamine, in a solvent such as dimethylformamide. The reaction with an acid anhydride may be carried out in the absence or presence of solvent such as pyridine.

Formylation may be effected by heating the aminotriazole (III) in dimethylformamide in the presence of a base, e.g. sodium hydride.

In the reaction with an isocyanate or isothiocyanate compounds of formula (I) in which $R_{10}$ is other than hydrogen or conveniently prepared by carrying out the reaction in a solvent such as acetonitrile at an elevated temperature, e.g. reflux. Compounds of formula (I) in which $R_{10}$ is hydrogen may be prepared by heating the aminotriazole (III) with an appropriate organic isocyanate or isothiocyanate such as ethylcarbonisothiocyanatidate, at an elevated temperature followed by hydrolysis of the resulting ester, for example with a base such as aqueous ethanolic sodium hydroxide.

In the following examples temperatures are in °C. "T.l.c." refers to thin layer chromatography carried out on silica using, unless otherwise stated, one of the following solvent systems:

| System A | methanol:0.88 ammonia (79.1) |
|---|---|
| System B | ethyl acetate:water:isopropanol: 0.88 ammonia (25:8:15:2) |
| System C | ethyl acetate:ethanol: 0.88 ammonia (20:3:2) |

Preparative chromatography was carried out on silica using methanol as eluant unless otherwise stated.

EXAMPLE 1

N-[5-[[3-[3-[(dimethylamino)methyl]phenoxy]propyl]amino]-1-methyl-1H-1,2,4-triazole-3-yl]-N'-methylthiourea A solution of 1-methyl-$N^5$-[3-[3-[(dimethylamino)methyl]phenoxy]propyl]-1H-1,2,4-triazole-3,5-diamine (A) (1.0 g) and methyl isothiocyanate (0.24 g) in dry acetonitrile was heated under reflux for 48 hours. The solvent was removed and the residual oil purified by column chromatography. The residue was dissolved in ethyl acetate. A solution of tartaric acid in ethyl acetate was added to give the title compound as the tartrate salt as a white powder (0.22 g). tlc System A $R_f$ 0.51. NMR (free base) CDCl$_3$, 0.4 brs. (1H); 2.78 t (1H); 3.0–3.3 m (3H); 4.77 t (1H); 5.90 t (2H); 6.46 s+q (5H); 6.60 s (2H); 6.80 d (3H); 7.76 s (6H); 7.90 m (2H).

The following compounds were similarly prepared from the appropriate aminotriazole and isocyanate.

(b) Aminotriazole (1.0 g) and methylisocyanate (0.2 g) gave N-[5-[[3-[3-[(dimethylamino)methyl]phenoxy]propyl]amino]-1-methyl-1H-1,2,4-triazol-3-yl]-N'-methylurea tartrate (1.2 g). tlc System A, $R_f$ 0.55. Nmr (free base) (CD Cl$_3$) 1.48,s, (1H); 2.10,q, (1H); 2.77,t, (1H); 3.0–3.3,m, (3H); 5.0,t, (1H); 5.9,t, (2H); 6.43,q, (2H); 6.48,s, (3H); 6.62,s, (2H); 7.15,d, (3H); 7.77,s, (6H); 7.9,m, (2H).

(c) 1-methyl-$N^5$-[3-[3-(1-piperdinylmethyl)phenoxy]propyl]-1H-1,2,4-triazole3,5-diamine (B) (1.5 g) and phenylisocyanate (0.52 g) gave N-[5-[[3-[3-(1-piperidinylmethyl)phenoxy]propyl]amino]-1-methyl-1H-1,2,4-triazol-3-yl]-N'-phenylurea (1.07 g) m.p. 137°–9° (from ethyl acetate) tlc System A, $R_f$ 0.57.

(d) Aminotriazole (B) (1.5 g) and cyclohexylisocyanate (0.64 g) gave N-[5-[[3-[3-(1-piperidinylmethyl)phenoxy]propyl]amino]-1-methyl-1H-1,2,4-triazol-3-yl]-N'cyclohexylurea (0.43 g) m.p. 129°–130° (from cyclohexane). tlc System B, $R_f$ 0.6.

(e) 1-methyl-$N^5$-[2-[[[5-[(dimethylamino)methyl]-4-methyl-2-furanyl]methyl]thio]ethyl]-1H-1,2,4-triazole- 3,5-diamine (1 g) and phenylisocyanate (0.35 ml) gave N-[5-[[2-[[[5-[(dimethylamino)methyl]-4-methyl-2-furanyl]methyl]thio]ethyl]amino]-1-methyl-1H-1,2,4-triazol-3-yl]-N'-phenylurea (0.65 g) m.p. 166°-7° (from acetonitrile/methanol) tlc System A: (79.1) R$_f$0.5.

(f) 1-methyl-N$^5$-[2-[[[5-[(dimethylamino)methyl]-2-furanyl]methyl]thio]ethyl]-1H-1,2,4-triazole-3,5-diamine (3.1 g) and methyl isocyanate (0.97 g) gave N-methyl-N'-[1-methyl-5-[[2-[[[5-[(dimethylamino)methyl]-2-furanyl]methyl]thio]ethyl]amino]-1H-1,2,4-triazole-3-yl]urea as a gum (2.5 g) tlc. System C R$_f$0.41. N.m.r. (CDCl$_3$) 1.70,s, (1H); 2.15, br q) (1H); 3.92,s, (2H); 5.06, t, (1H); 6.52,s, (3H); 6.63, s+q, (4H), 7.20,d+t, (5H); 7.80,s, (6H).

EXAMPLE 2

Ethyl 1-methyl-5-[[3-[3-(N,N-dimethylaminomethyl)phenoxy]propyl]amino]-1H-1,2,4-triazole-3-carbamate, tartrate A solution of ethyl chloroformate (0.6 ml) and 1-methyl-N$^5$-[3-[3-(N,N-dimethylaminomethyl)phenoxy]propyl]-1H-1,2,4-triazole-3,5-diamine (2.0 g) in dry dimethylformamide (30 ml) was stirred at 25° for 12 h. The reaction mixture was diluted with water and extracted with ethyl acetate. The organic extracts were evaporated to leave a yellow oil which was triturated with a mixture of ether, ethyl acetate and light petroleum (b.p. 60°-80°). Insoluble material was filtered off and the residual oil dissolved in ethyl acetate. A saturated solution of tartaric acid in ethyl acetate was added until no more precipitate was formed, to give the title compound as a white solid (0.88 g) m.p. 110°-115° tlc System A, R$_f$0.61.

(b) Similarly prepared from 1-methyl-N$^5$-[3-[3-(1-piperidinylmethyl)phenoxy]propyl]-1H-1,2,4-triazole-3,5-diamine (5 g) and ethyl chloroformate (1.56 g) was ethyl [1-methyl-5-[[3-[3-(1-piperidinylmethyl)phenoxy]propyl]amino]-1H-1,2,4-triazol-3-yl]carbamate tartrate (0.85 g) m.p. 82° N.m.r. (D$_2$O) 2.51,m, (1H); 2.7-3.1,m, (3H); 5.42,s, (2H); 5.5-6,m, (6H); 6.3-6.7 m+s, (7H); 6.8-7.3, m, (2H); 7.6-8.6,m, (8H); 8.71,t, (3H).

EXAMPLE 3

(a) N-[5-[[3-[3-[(dimethylamino)methyl]phenoxy]propyl]amino]-1-methyl-1H-1,2,4-triazol-3-yl]acetamide, tartrate Acetic anhydride (0.35 g) was added dropwise to a solution of 1-methyl-N$^5$-[3-[3-[(dimethylamino)methyl]phenoxy]propyl]-1H-1,2,4-triazole-3,5-diamine (A) (1 g) in dry pyridine and the reaction was stirred at 25° for 12 h. Solvent was removed and the residue was dissolved in ethyl acetate, washed with aqueous saturated sodium carbonate solution, dried and evaporated. The residual oil was purified by chromatography and treated with a solution of tartaric acid in ethyl acetate to give the title compound (1.2 g) m.p. 103°-6° tlc System A, R$_f$0.5.

The following compounds were similarly prepared from the appropriate diamine:

(b) 1-methyl-N$^5$-[3-[3-(1-piperidinylmethyl)phenoxy]propyl]-1H-1,2,4-triazole-3,5-diamine (B) (2.5 g) and acetic anhydride (0.75 g) gave N-[5-[[3-[3-[(1-piperidinylmethyl)phenoxy]propyl]amino]-1-methyl-1H-1,2,4-triazole-3-yl]acetamide, tartrate (2.7 g) m.p. 90° (softens) tlc System A, R$_f$0.6.

(c) Diamine (B) (1.0 g) and methanesulphonic anhydride (0.59 g) gave 5-[[3-[3-(1-piperidinylmethyl)phenoxy]propyl]amino]-1-methyl-1H-1,2,4-triazole-3-sulphamic acid, methyl ester, methane sulphonate (1.2 g) m.p. 130°-1°. tlc system A, R$_f$0.54.

(d) Diamine (A) (1 g) and benzoic anhydride (0.8 g) gave N-[5-[[3-[3-[(dimethylamino)methyl]phenoxy]propyl]amino]-1-methyl-1H-1,2,4-triazol-3-yl]benzamide, tartrate (0.48 g) m.p. 126°-130°. tlc System A, R$_f$ 0.47.

(e) 1-methyl-N$^5$-[2-[[[5-[(dimethylamino)methyl]-2-furanyl]methyl]thio]ethyl]-1H-1,2,4-triazole-3,5-diamine (1.9 g) and benzoic anhydride (1.2 g) gave N-[1-methyl-5-[[2-[[[5-[(dimethylamino)methyl]-2-furanyl]methyl]thio]ethyl]amino]-1H-1,2,4-triazol-3yl]benzamide (0.95 g). tlc System C, R$_f$0.45.

Found: C, 57.7; H, 6.4; N, 19.8; C$_{20}$H$_{26}$N$_6$O$_2$S requires C, 58.0; H, 6.3; N, 20.3%.

(f) 1-methyl-N$^5$-[2-[[[5-[(dimethylamino)methyl]-4-methyl-2-furanyl]methyl]thio]ethyl]-1H-1,2,4-triazole-3,5-diamine (0.96 g) and benzoic anhydride (1.0 g) gave N-[1-methyl-5-[[2-[[[5-[(dimethylamino)methyl]-4-methyl-2-furanyl]methyl]thio]ethyl]amino]-1H-1,2,4-triazol-3-yl]benzamide (0.6 g). tlc System C, R$_f$ 0.42 N.m.r. (CDCl$_3$) 0.90,s, (1H); 2.10,m, (2H); 2.5,m, (3H); 4.06,s, (1H); 5.10,t, (1H); 6.43,s, (2H); 6.52,s, (3H); 6.68,s+q, (4H); 7.32,t, (2H); 7.82,s, (6H); 8.10,s, (3H).

(g) 1-methyl-N$^5$-[2-[[[5-[(dimethylamino)methyl]-2-thienyl]methyl]thio]ethyl]-1H-1,2,4-triazole-3,5-diamine (0.98 g) and benzoic anhydride (1.0 g) gave N-[1-methyl-5-[[2-[[[5-[(dimethylamino)methyl]-2-thienyl]methyl]thio]ethyl]amino]-1H-1,2,4-triazol-3-yl]benzamide (0.5 g). tlc System C, R$_f$ 0.46. N.m.r. (CDCl$_3$) 1.02,br.s, (1H); 2.07,m, (2H); 2.5,m, (3H); 3.30,m, (2H); 5.43,t, (1H); 6.18,s, (2H); 6.5,2s+q, (7H); 7.28,t, (2H); 7.77,s, (6H).

EXAMPLE 4

N-[1-methyl-5-[[3-[3-(1-piperidinylmethyl)phenoxy]propyl]amino]-1H-1,2,4-triazol-3-yl]formamide A mixture of sodium hydride (0.72 g) and 1-methyl-N$^5$-[3-[3-(1-piperidinylmethyl)phenoxy]propyl]-1H-1,2,4-triazole-3,5-diamine (3.44 g) in dimethylformamide (50 ml) was heated under reflux for 8 h. The reaction mixture was cooled, poured onto water (300 ml) and extracted with ether. Evaporation of the organic extract gave a yellow oil, which was extracted with boiling cyclohexane (500 ml). As the cyclohexane extract was cooled a brown oil precipitated out. This oil was discarded and the supernatant solution was cooled to room temperature to give the title compound which was recrystallised from a mixture of ethyl acetate and light petroleum (b.p. 60°-80°) as a pale yellow solid (0.35 g) m.p. 68°-75° (decomposition). tlc, System C: R$_f$0.6.

EXAMPLE 5

N-[1-methyl-5-[[2-[[[5-[(dimethylamino)methyl]-2-furanyl]methyl]thio]ethyl]amino]-1H-1,2,4-triazol-3-yl]formamide A stirred suspension of 1-methyl-N$^5$-[2-[[[5-(dimethylamino)methyl-2-furanyl]methyl]thio]ethyl]-1H-1,2,4-triazole-3,5-diamine, dihydrochloride (3.83 g) and potassium carbonate (3.04 g) in acetone (60 ml) was heated at reflux for 30 min, and then cooled to 5° C. Aceticformic anhydride (1.32 g) was added and the suspension was allowed to warm up to room temperature. The inorganic material was filtered off and the solution evaporated to give an oil which was chromatographed. The resulting oil was dissolved in ethyl acetate, washed with saturated aqueous sodium bicarbonate and evaporated to afford the title compound (0.47 g)

as a colourless oil. tlc System B, $R_f$ 0.61. Nmr. (CDCl$_3$) 0.28 brd, (1H); 0.93 d, (1H); 3.81,s, (2H); 5.25, brt (1H); 6.28,s, (2H); 6.47,s, (3H); 6.52 s+m (2H); 7.16,t, (2H) 7.74,s, (6H).

EXAMPLE 6

N-[1-methyl-5-[[3-[3-(1-piperidinylmethyl)phenoxy]-propyl]amino]-1H-1,2,4-triazol-3-yl]-2-furancarboxamide A solution of 1-methyl-N$^5$-[3-[3-(1-piperidinylmethyl)phenoxy]propyl]-1H-1,2,4-triazole-3,5-diamine (A) (1.0 g) and 2-furancarboxylic acid, chloride (0.42 g) in pyridine (25 ml) was kept at ambient temperature for 1 h. The pyridine was evaporated in vacuo and the residue was azeotropically distilled with toluene to give an oil which was partitioned between ethyl acetate and 2 M hydrochloric acid. The pH of the aqueous extract was adjusted to pH 9 and it was extracted with ethyl acetate. The organic extracts were evaporated to a gum which was chromatographed on silica using ethyl acetate: methanol (9:1) to give the title compound (0.30 g) as a glassy solid. tlc System B, $R_f$ 0.57. Nmr (CDCl$_3$) 1.5,brs, (1H); 2.53,m, (1H); 2.75,t+m, (2H); 3.0–3.3,m, (3H); 3.5,dd (1H); 5.31,t, (1H); 5.92,t, (2H); 6.42,q, (2H); 6.50,s, (3H); 6.59,s, (3H); 7.6,brs; (4H); 7.9,m, (2H); 8.5,m, (6H).

(b) Similarly prepared from diamine (A) (1 g) and 3-pyridinecarboxylic acid, chloride, hydrochloride (0.57 g) was N-[1-methyl-5-[[3-[3-(1-piperidinylmethyl)-phenoxy]propyl]amino]-1H-1,2,4-triazol-3-yl]-3-pyridinecarboxamide (0.98 g). tlc System B, $R_f$ 0.64. Nmr (CDCl$_3$) 0.85,d, (1H); 1.07,brs, (1H); 1.22,dd (1H); 1.78,m, (1H); 2.62,q, (1H); 2.77,t, (1H); 3.0–3.3,m, (3H); 5.35,t, (1H); 5.92,t, (2H); 6.48,s, (3H); 6.50,m (2H) 6.55,s, (2H); 7.5–7.7,m, (4H); 7.90,m, (2H); 8.3–8.6,m, (6H).

The following compounds were similarly prepared from the appropriate aminotriazole and acid chloride (c) The triazole (A) (2.00 g) and 4-methoxybenzoic acid, chloride (1.10 g) gave 4-methoxy-N-[1-methyl-5-[[3-[3-(1-piperidinylmethyl)phenoxy]propyl]amino]-1H,1,2,4-triazol-3-yl]benzamide (2.00 g), m.p. 93.5°–97°. tlc. System B $R_f$ 0.78

Found: C, 65.0; H, 7.0; N.17.0; C$_{26}$H$_{34}$N$_6$O$_3$ requires: C, 65.2; H, 7.1; N,17.5%.

(d) The triazole (A) (2.00 g) and 4-methylbenzenesulphonic acid, chloride (1.22 g) was 4-methyl-N-[1-methyl-5-[[3-[3-(1-piperidinylmethyl)phenoxy]propyl]amino]-1H-1,2,4-triazol-3-yl]benzenesulphonamide (1.58 g) m.p. 100.5°–102°.

Found: C, 57.1; H,6.7;N,15.7; C$_{25}$H$_{34}$N$_6$O$_3$S·$\frac{2}{3}$H$_2$O requires C,57.1; H,7.1;N,16.0%.

EXAMPLE 7

Following the method of Example 1, 1-methyl-N$^5$-[2-[[[5-[(dimethylamino)methyl]-2-thienyl]methyl]thio]ethyl]-1H-1,2,4-triazole-3,5-diamine (0.67 g) and methyl isocyanate (0.17 ml) gave N-[5-[[2-[[[5-[(dimethylamino)methyl]-2-thienyl]methyl]thio]ethyl]amino]-1-methyl-1H-,2,4-triazol-3-yl]-N'-methyl urea (0.4 g). N.m.r. (CDCl$_3$): 3.23,q, (2H); 6.02,s, (2H); 6.4–6.5,s+s+t, (7H); 7.1–7.2,s+s, (5H); 7.75,s, (6H). T.l.c. System B $R_f$ 0.55.

EXAMPLE 8

The following compounds were prepared using the method of Example 3:

(a) 1-methyl-N$^5$-[2-[[[-5-[(dimethylamino)methyl]-2-thienyl]methyl]thio]ethyl]-1H-1,2,4-triazole-3,5-diamine (0.5 g) and methane sulphonic anhydride (0.3 g) gave N-[1-methyl-5-[[2-[[[5-[(dimethylamino)methyl]-2-thienyl]methyl]thio]ethyl]amino]-1H-1,2,4-triazol-3-yl]methane sulphonamide (0.05 g). N.m.r. (CDCl$_3$): 3.22,q, (2H); 4.28,t, (1H); 6.10,s,s (2H); 6.4–6.5,m, (7H); 6.80,s, (ca 3H); 7.28,t, (2H); 7.33,s,s (6H). T.l.c. System B $R_f$ 0.25.

(b) 1-methyl-N$^5$-[2-[[[5-[(dimethylamino)methyl]-2-furanyl]methyl]thio]ethyl]-1H-1,2,4-triazole-3,5-diamine (1.55 g) and acetic anhydride (0.5 g) gave N-[1-methyl-5-[[2-[[[5-[(dimethylamino)methyl]-2-furanyl]-methyl]thio]ethyl]amino]-1H,1,2,4-triazol-3-yl]acetamide, oxalate (1.3 g) m.p. 132°–4°.

N.m.r. (D$_2$O): 3.30,d, (1H); 3.60,d, (1H); 5.67,s, (2H); 6.13s, (2H); 6.45, s+t, (5H); 7.15,s+t, (8H) 7.80,s, (3H).

(c) 1-methyl-N$^5$-[2-[[[5-[(dimethylamino)methyl]-4-methyl-2-furanyl]methyl]thio]ethyl]-1H-1,2,4-triazole-3,5-diamine (1 g) and acetic anhydride (0.32 ml) gave N-[1-methyl-5-[[2-[[[5-[(dimethylamino)methyl]-4-methyl-2-furanyl]methyl]thio]ethyl]amino]-1H-1,2,4-triazol-3-yl]acetamide (0.5 g).

T.l.c. System B $R_f$ 0.4.

N.m.r. (CDCl$_3$): 1.2,br.s. (1H); 4.05,s, (1H); 5.2,t, (1H); 6.4,s, (2H); 6.5–6.7,m, (7H); 7.25,t, (2H); 7.75,s, (9H); 8.10,s, (3H).

(d) 1-methyl-N$^5$-[3-[4-(1-piperidinylmethyl)phenoxy]-propyl]-1H-1,2,4-triazole-3,5-diamine (0.5 g) and acetic anhydride (157 mg) gave 1-methyl-N-[5-[[3-[4-(1-piperidinylmethyl)phenoxy]propyl]amino]-1H-1,2,4-triazol-3-yl]acetamide (0.58 g).

N.m.r. (CDCl$_3$): 2.75,d, (2H); 3.18,d, (2H); 5.95,t, (2H); 6.4–6.7,m, (2H); 6.55,s, (3H); 6.60,s, (2H) 7.5–8.1,m, (6.H); 7.87,s, (3H); 8.3–8.7 m, (6H).

T.l.c. System A, $R_f$ 0.52.

EXAMPLE 9

The following compounds were prepared using the method of Example 6:

(a) 1-methyl-N$^5$-[3-[3-(1-piperidinylmethyl)phenoxy]-propyl]-1H-1,2,4-triazole-3,5-diamine (A) (2.00 g) and phenylacetylchloride (0.99 g) gave N-[1-methyl-5-[[3-[3-(1-piperidinylmethyl)phenoxy]propyl]amino]-1H-1,2,4-triazol-3-yl]benzeneacetamide (0.92 g).

N.m.r. (CDCl$_3$): 1.9,br,s, (1H); 2.70,2.80,s+t, (6H); 3.0–3.3,m, (3H); 5.30,t, (1H); 5.98,t, (2H); 6.28,br.s, (2H) 6.55,s+s+q, (7H); 7.65; m, (4H); 8.0,m, (2H); 8.5,m, (6H).

T.l.c. System B, $R_f$ 0.71.

(b) The triazole (A) (2.00 g) and benzoyl chloride (0.90 g) gave N-[1-methyl-5-[[3-[3-(1-piperidinylmethyl)phenoxy]propyl]amino]-1H-1,2,4-triazole-3-yl]benzamide (1.05 g).

N.m.r. (CDCl$_3$): 0.9,br,s, (1H); 2.00–2.25,m, (2H); 2.4–2.7,2.8,m+t, (4H); 3.00–3.35,m, (3H); 5.22,t, (1H) 5.98,t, (2H); 6.50,6.55,6.60,s+s+q, (7H); 7.60,m, (4H) 8.0,m, (2H); 8.5,m, (6H);

Found: C, 66.77; H, 7.30; N,18.72; C$_{25}$H$_{32}$N$_6$O$_2$ requires: C, 66.94; H, 7.19; N,18.74%

EXAMPLE 10

N-methyl-N'-[1-methyl-5-[[3-[3-(1-piperidinylmethyl)phenoxy]propyl]amino]-1H-1,2,4,-triazol-3-yl]urea A mixture of 1-methyl-N$^5$-[3-[3-(1-piperidinylmethyl)phenoxy]propyl]-1H-1,2,4-triazole-3,5-diamine (2.00 g) and methylisocyanate (1.2 g) in dry acetonitrile (60 ml) was heated at reflux for 2 h. and allowed to cool. The precipitated solid was collected and recrystallised from methanol to give the title compound (1.9 g).

T.l.c. System B: $R_f$ 0.71.

N.m.r. (CDCl$_3$): 1.22,s, (1H); 2.07,q, (1H); 2.78,t, (1H); 3.00–3.30,m, (3H); 4.90,t, (1H); 5.90,t, (2H); 6.42,6.48, 6.58,q+s+s, (7H); 7.10,d, (3H); 7.60,7.90,m+m, (6H); 8.50,m, (6H).

EXAMPLE 11

Ethyl-[5-[[2-[[[5-[(dimethylamino)methyl]-2-thienyl]-methyl]thio]ethyl]amino]-1-methyl-1H-1,2,4-triazole-3-yl]carbamate A cooled mixture of ethylchloroformate (0.45 g) in pyridine was treated with a solution of N$^5$-[2-[[[5-[(dimethylamino)methyl]-2-thienyl]methyl]thio]ethyl]-1-methyl-1H-1,2,4-triazole-3,5-diamine (0.7 g) in pyridine (8 ml). Sodium carbonate (2 g) and water (10 ml) were added and the mixture evaporated in vacuo. The residue was dissolved in water (15 ml) and extracted with hot isopropanol (30 ml). The extract was evaporated and the residue purified by column chromatography (silica:methanol:0.88 ammonia; 79:1) to give the title compound (0.48 g).

T.l.c. System A $R_f$ 0.6.

N.m.r. (CDCl$_3$) 1.8,brs (1H); 3.25,m, (2H); 5.47,brt (1H); 5.88,q, (2H); 6.13,s, (2H); 6.47,2s+q, (7H); 7.24,t, (2H); 7.75,s, (6H); 8.73,t, (3H).

EXAMPLE 12

N-[5-[[4-[5-[(Dimethylamino)methyl]-2-furanyl]-butyl]amino]-1-methyl-1H-1,2,4-triazol-3-yl]-N$^1$-phenyl urea N$^5$-[4-[5-[(Dimethylamino)methyl]-2-furanyl]butyl]1-methyl-1H-1,2,4-traizole-3,5-diamine A mixture of N-cyano-1-methyl-2-(phenylmethylene)-hydrazine carboximidothioic acid methyl ester (2.32 g) and 4-[5-[(dimethylamino)methyl]-2-furanyl]-butanamine (1.96 g) was heated at 60° under reduced water-pump pressure for 1 h. The residual oil was used without further purification, and stirred with 2 N hydrochloric acid (10 ml) for 0.5 h. The pH of the acidic solution was adjusted to pH 9 with potassium carbonate, and washed with toluene. An excess of potassium carbonate was added to the aqueous phase which was then extracted with ethyl acetate. The organic extracts were dried and evaporated to give a solid which was recrystallised from ethyl acetate to give the title compound as a white solid (2.1 g), m.p. 105° C.

Using the method of Example 1.

N$^5$-[4-[5-[(Dimethylamino)methyl]-2-furanyl]butyl]-1-methyl-1H-1,2,4-triazole-3,5-diamine (0.73 g) and phenylisocyanate (0.25 ml) gave N-[5-[[4-[5-[(dimethylamino)methyl]-2-furanyl]butyl]amino]-1-methyl-1H-1,2,4-triazol-3-yl]-N$^1$-phenyl urea (0.67 g), m.p. 124–5°. T.l.c. system C. $R_f$ 0.42.

Examples of Pharmaceutical compositions according to the invention are as follows:

| (a) TABLETS | mg/tablet | mg/tablet |
|---|---|---|
| Active ingredient | 20.0 | 40.0 |
| Microcrystalline cellulose BPC | 99.5 | 199.0 |
| Magnesium stearate B.P. | 0.5 | 1.0 |
| Compression weight | 120.0 | 240.0 |

The drug is sieved through a 250 μm sieve, blended with the excipients and compressed using 6.5 mm and 8.0 mm diameter punches for the 20 and 40 mg strengths respectively. Tablets of other strengths may be prepared by increasing the compression weight and using punches to suit.

The tablets may be film coated with suitable film forming materials, e.g. methyl cellulose, ethyl cellulose or hydroxypropylmethyl cellulose, using standard techniques. Alternatively the tablets may be sugar coated.

| (b) CAPSULES | mg/capsule |
|---|---|
| Active ingredient | 20.0 |
| **Sta-Rx 1500 Starch | 79.5 |
| Magnesium Stearate B.P. | 0.5 |
| Fill weight | 100.0 |

**A form of directly compressible starch supplied by Colorcon Ltd, Orpington, Kent.

The active ingredient is sieved through a 250 μm sieve and blended with other materials. The mix is filled into No. 3. hard gelatin capsules using a suitable filling machine. Other doses may be prepared by increasing the fill weight and if necessary changing the capsule size to accommodate the increase.

| (c) SUSTAINED RELEASE TABLETS | mg/tablet |
|---|---|
| Active ingredient | 80 |
| *Cutina HR | 25 |
| Lactose B.P. | 142.5 |
| Magnesium Stearate B.P. | 2.5 |
| Compression weight | 250.0 |

*Cutina HR is a grade of microfine hydrogenated castor oil supplied by Sipon Products Ltd., London.

The drug is sieved through a 250 μm sieve and blended with the Cutina HR and lactose. The mixed powders are moistened with Industrial Methylated Spirits 74 O.P., granules are made, dried, screened and blended with the magnesium stearate. The lubricated granules are compressed using 8.5 mm punches to produce tablets with a hardness of not less than 10 Kp (Schleuniger tester).

| (d) INJECTION FOR INTRAVENOUS ADMINISTRATION | % w/v |
|---|---|
| Active ingredient | 0.25 |
| Water for Injections BP to | 100.00 |

Sodium chloride may be added to adjust the tonicity of the solution and the pH may be adjusted to that of maximum stability using either dilute acid or alkali.

The solution is prepared, clarified and filled under nitrogen into appropriate sized ampoules sealed by fusion of the glass. The injection is sterilised by heating in an autoclave using one of the acceptable cycles. Alternatively the solution may be sterilized by filtration and filled into sterile ampoules under aseptic conditions.

| (e) SYRUP | mg/5ml dose |
|---|---|
| Active ingredient | 20.0 mg |
| Sucrose | 2750.0 mg |
| Glycerine | 500.0 mg |
| Buffer Flavour Colour Preservative | as necessary |
| Distilled water to | 5.0 ml |

The active ingredient, buffer, flavour, preservative and colour are dissolved in some of the water. The remainder of the water is heated to approximately 80° C. and the sucrose is dissolved in this and cooled. The two solutions are mixed, adjusted to volume and clarified by filtration.

We claim:

1. A compound of the formula (I)

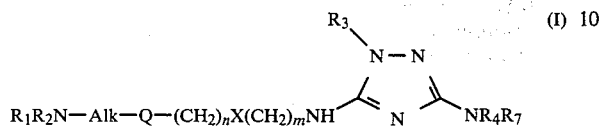

and physiologically acceptable acid addition salts and hydrates thereof, in which $R_1$ and $R_2$ which may be the same or different, each represent hydrogen, $C_{1-10}$ alkyl, $C_{3-18}$ cycloalkyl, $C_{3-6}$ alkenyl, $C_{3-6}$ alkynyl, phenyl $C_{1-6}$ alkyl, substituted phenyl $C_{1-6}$ alkyl wherein said substituent is at least one $C_{1-3}$ alkyl or $C_{1-6}$ alkoxy groups or halogen atoms; trifluoro $C_{1-6}$ alkyl, or $C_{1-6}$ alkyl substituted by hydroxy, $C_{1-6}$ alkoxy, amino, $C_{1-6}$ alkylamino, di-$C_{1-6}$ alkylamino or $C_{3-8}$ cycloalkyl or $R_1$ and $R_2$ may together with the nitrogen atom to which they are attached form a heterocyclic ring which is pyrrolidine, piperidine optionally substituted in the 4-position by methyl or hydroxy, tetrahydropyridine, morpholine, 2,6-dimethylmorpholine, hexamethyleneimine or heptamethyleneimine;

Alk represents a straight or branched alkylene chain of 1 to 6 carbon atoms;

Q represents a furan or thiophene ring in which incorporation into the rest of the molecule is through bonds at the 2- and 5-positions, the furan ring optionally bearing a further substituent $R_6$ adjacent to the group $R_1R_2N$-Alk-, or Q represents a benzene ring in which incorporation into the rest of the molecule is through bonds at the 1- and 3- or 1- and 4-positions;

$R_6$ represents halogen or $C_{1-4}$ alkyl which may be substituted by hydroxy or $C_{1-4}$ alkoxy;

X represents $-CH_2-$, $-O-$, $-S-$ or

where $R_5$ represents hydrogen or methyl;

n represents zero, 1 or 2;

m represents 2, 3 or 4;

$R_3$ represents hydrogen, $C_{1-6}$ alkyl, $C_{3-6}$ alkenyl, phenyl $C_{1-6}$ alkyl, substituted phenyl $C_{1-6}$ alkyl wherein said substituent is at least one $C_{1-3}$ alkyl or $C_{1-6}$ alkoxy groups or halogen atoms; hydroxy $C_{2-6}$ alkyl; $C_{1-6}$ alkoxy $C_{1-6}$ alkyl, or phenyl, substituted phenyl wherein said substituent is at least one $C_{1-3}$ alkyl or $C_{1-6}$ alkoxy groups or halogen atoms; and $R_4$ represents hydrogen, $C_{1-6}$ alkyl, $C_{3-6}$ alkenyl or phenyl $C_{1-6}$ alkyl, substituted phenyl $C_{1-6}$ alkyl wherein said substituent is at least one $C_{1-3}$ alkyl or $C_{1-6}$ alkoxy groups or halogen atoms, and $R_7$ represents the group $COR_8$ where $R_8$ represents hydrogen, $C_{1-6}$ alkyl, phenyl, substituted phenyl wherein said substituent is at least one $C_{1-3}$ alkyl or $C_{1-6}$ alkoxy groups or halogen atoms; phenyl $C_{1-6}$ alkyl, substituted phenyl $C_{1-6}$ alkyl wherein said substituent is at least one $C_{1-3}$ alkyl or $C_{1-6}$ alkoxy groups or halogen atoms; $C_{1-6}$ alkoxy, heteroaryl, wherein said heteroaryl is furyl, pyridyl, thiazolyl, quinolinyl, indolyl or thienyl; or monocyclic heteroaryl $C_{1-6}$ alkyl wherein said monocyclic heteroaryl portion is furyl, pyridyl, thiazolyl, or thienyl, or $R_7$ represents the group $SO_2R_9$ where $R_9$ represents $C_{1-6}$ alkyl or phenyl, substituted phenyl wherein said substituent is at least one $C_{1-3}$ alkyl or $C_{1-6}$ alkoxy groups or halogen atoms, or $R_7$ represents the group

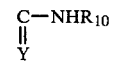

where Y is oxygen or sulphur and $R_{10}$ represents hydrogen, $C_{1-6}$ alkyl, $C_{3-8}$ cycloalkyl, phenyl, substituted phenyl wherein said substituent is at least one $C_{1-3}$ alkyl or $C_{1-6}$ alkoxy groups or halogen atoms, or phenyl $C_{1-6}$ alkyl, substituted phenyl $C_{1-6}$ alkyl wherein said substituent is at least one $C_{1-3}$ alkyl or $C_{1-6}$ alkoxy groups or halogen atoms.

2. A compound according to claim 1 in which $R_1$ and $R_2$ are as defined in claim 1 except $C_{3-6}$ alkynyl or $C_{1-6}$ alkyl substituted by $C_{3-8}$ cycloalkyl; and $R_4$ and $R_7$ are as defined in claim 1 except that $R_8$ is other than heteroaryl and $R_{10}$ is other than $C_{3-8}$ cycloalkyl; provided that when X represents an oxygen atom or $-NR_5-$ and when n is zero then Q represents benzene.

3. A compound according to claim 1 in which Q represents benzene incorporated into the molecule through bonds at the 1- and 3-positions, n is zero and X is oxygen.

4. A compound according to claim 1 in which m+n is 3 or 4.

5. A compound according to claim 1 in which Alk is $-CH_2-$.

6. A compound according to claim 1 in which $R_1$ represents hydrogen or $C_{1-4}$ alkyl and $R_2$ represents $C_{3-5}$ alkenyl, $C_{5-7}$ cycloalkyl, benzyl, $C_{1-8}$ alkyl or $C_{1-4}$ alkyl substituted by $C_{1-3}$ alkoxy, hydroxy, di-$C_{1-3}$ alkylamino or trifluoromethyl or $R_1$ and $R_2$ together with the nitrogen atom to which they are attached form a heterocyclic ring which is pyrrolidine, piperidine optionally substituted in the 4-position by methyl or hydroxy, tetrahydropyridine, morpholine, 2,6-dimethylmorpholine, hexamethyleneimine or heptamethyleneimine.

7. A compound according to claim 6 in which $R_1$ and $R_2$ represent $C_{1-3}$ alkyl, or $R_1$ and $R_2$ together with the nitrogen atom to which they are attached form a heterocyclic ring which is pyrrolidine, piperidine optionally substituted in the 4-position by methyl or hydroxy, tetrahydropyridine, morpholine, 2,6-dimethylmorpholine, hexamethyleneimine or heptamethyleneimine.

8. A compound according to claim 1 wherein $R_3$ represents hydrogen, $C_{1-6}$ alkyl or $C_{2-4}$ hydroxyalkyl.

9. A compound according to claim 1 wherein the group $NR_4R_7$ represents the group $NHCOR_8$ where $R_8$ represents hydrogen, $C_{1-6}$ alkyl, phenyl, substituted phenyl wherein said substituent is at least one $C_{1-3}$ alkyl or $C_{1-6}$ alkoxy groups or halogen atoms; heteroaryl, wherein said heteroaryl is furyl, pyridyl, thiazolyl, or thienyl; or $C_{1-6}$ alkoxy; or the group $NHCONHR_{10}$ where $R_{10}$ represents $C_{1-6}$ alkyl, phenyl, substituted phenyl wherein said substituent is at least one $C_{1-3}$ alkyl or $C_{1-6}$ alkoxy groups or halogen atoms, or $C_{3-8}$ cycloalkyl.

10. A compound according to claim 9 in which the group $NR_4R_7$ represents the group $NHCOR_8$ where $R_8$ is hydrogen, phenyl, substituted phenyl wherein said substituent is at least one $C_{1-3}$ alkyl or $C_{1-6}$ alkoxy groups or halogen atoms; $C_{1-6}$ alkyl or $C_{1-6}$ alkoxy, or the group $NHCONHR_{10}$ where $R_{10}$ is phenyl, substituted phenyl wherein said substituent is at least one $C_{1-3}$ alkyl or $C_{1-6}$ alkoxy groups or halogen atoms.

11. A compound according to claim 1 corresponding to the formula (II)

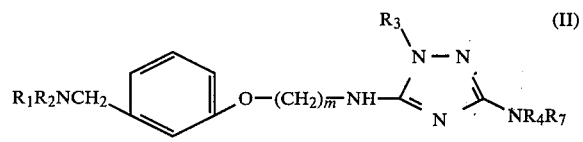

where $R_1$ and $R_2$ are methyl groups or together with the nitrogen atom to which they are attached form a pyrrolidino, piperidino or hexamethyleneimino group; m is 3 or 4; $R_3$ is hydrogen or methyl, and $NR_4R_7$ is a formamido, $C_{2-7}$ alkanoylamino, $C_{1-6}$ alkoxycarbonylamino, aroylamino wherein the aryl portion of the aroylamino group is phenyl or substituted phenyl wherein said substituent is at least one $C_{1-3}$ alkyl or $C_{1-6}$ alkoxy groups or halogen atoms; or phenylcarbamoylamino group.

12. A compound according to claim 1 which is N-[1-methyl-5-[[3-[3-(1-piperidinylmethyl)phenoxy]propyl]amino]-1H-1,2,4-triazole-3-yl]formamide, N-[5-[[3-[3-(dimethylamino)methyl]phenoxy]propyl]amino-1-methyl-1H-1,2,4-triazole-3-yl]acetamide, or their physiologically acceptable acid addition salts.

13. A compound according to claim 1 which is ethyl 1-methyl-5-[[3-[3-[(dimethylamino)methyl]phenoxy]propyl]amino]-1H-1,2,4-triazole-3-carbamate, N-[5-[[3-[3-[(dimethylamino)methyl]phenoxy]propyl]amino]-1-methyl-1H-1,2,4-triazole-3-yl]benzamide, N-[5-[[3-[3-(1-piperidinylmethyl)phenoxy]propyl]amino]-1-methyl-1H-1,2,4-triazole-3-yl]-N'-phenylurea, or their physiologically acceptable acid addition salts.

14. A compound according to claim 1 in the form of a hydrochloride, hydrobromide, sulphate methanesulphonate, acetate, maleate, succinate, citrate, fumarate, benzoate or tartrate salt.

15. A pharmaceutical composition for the treatment of conditions mediated through $H_2$-receptors comprising an effective amount of at least one compound as claimed in any of claims 1 to 14 together with at least one pharmaceutically acceptable carrier or diluent.

16. A pharmaceutical composition according to claim 15 in a form adapted for oral administration.

17. A pharmaceutical composition according to claim 16 containing 5 mg to 1 g of the compound of formula (I).

18. A method of treating a condition mediated through histamine $H_2$-receptors which comprises administering to a patient an effective amount of a compound as defined in claim 1 to relieve said condition.

* * * * *